United States Patent [19]

Reed

[11] Patent Number: 4,526,672
[45] Date of Patent: Jul. 2, 1985

[54] OXYGEN SENSOR

[75] Inventor: Larry T. Reed, Richardson, Tex.

[73] Assignee: Axia Incorporated, Oak Brook, Ill.

[21] Appl. No.: 592,626

[22] Filed: Mar. 23, 1984

[51] Int. Cl.³ .................................................. G01N 27/46
[52] U.S. Cl. ..................................... 204/428; 204/427;
174/74 R; 174/75 F
[58] Field of Search ........................ 204/421, 424–429;
174/74 R, 75 R, 75 F

[56] References Cited

U.S. PATENT DOCUMENTS

| | | |
|---|---|---|
| 3,347,767 | 10/1967 | Hickman . |
| 3,442,773 | 5/1969 | Wilson . |
| 3,514,377 | 5/1970 | Spacil et al. . |
| 3,616,274 | 10/1971 | Eddy . |
| 3,768,259 | 10/1973 | Carnahan . |
| 3,819,500 | 6/1974 | Van Esdonk et al. . |
| 3,828,749 | 8/1974 | Knapp . |
| 3,844,920 | 10/1974 | Burgett et al. ................... 204/428 |
| 3,847,778 | 11/1974 | Riddel ................... 204/427 |
| 3,874,171 | 4/1975 | Schmidt et al. . |
| 3,960,692 | 6/1976 | Weyl et al. ................... 204/428 |
| 3,960,693 | 6/1976 | Weyl et al. ................... 204/428 |
| 4,033,170 | 7/1977 | Kawamura et al. . |
| 4,050,425 | 9/1977 | Holleboom . |
| 4,061,117 | 12/1977 | Ikeura . |
| 4,108,122 | 8/1978 | Barnard . |
| 4,123,131 | 10/1978 | Pearce et al. ................... 204/428 |
| 4,129,099 | 12/1978 | Howarth . |
| 4,132,615 | 1/1979 | Linder et al. ................... 204/15 |
| 4,169,778 | 10/1979 | Mann et al. ................... 204/429 |
| 4,175,019 | 11/1979 | Murphy ................... 204/429 |
| 4,178,222 | 12/1979 | Murphy et al. ................... 204/427 |
| 4,198,939 | 5/1980 | Masaki . |
| 4,222,840 | 9/1980 | Murphy et al. ................... 204/427 |
| 4,347,113 | 8/1982 | Fischer et al. ................... 204/428 |
| 4,359,989 | 11/1982 | Masaki et al. . |

FOREIGN PATENT DOCUMENTS 99064 7/1980 Japan ................... 204/428

Primary Examiner—T. Tung
Attorney, Agent, or Firm—Richards, Harris, Medlock & Andrews

[57] ABSTRACT

An exhaust gas sensor (10) is disclosed which includes a sensor element (12) and a member (48). The member (48) includes a hollow tube (50) and a seal disk (58). The seal disk (58) is urged into sealing engagement with an annular surface (14) on the sensor element (12) to prevent exhaust gas from entering the interior (26) of the sensor element (12). The inner electrode (22) of the sensor element (12) extends to the annular surface (14) in an annular ring (88). The seal disk (58) is permitted to contact the inner electrode (22) about the entire periphery of the ring (88).

6 Claims, 2 Drawing Figures

OXYGEN SENSOR

TECHNICAL FIELD

This invention relates to sensing of gas, and in particular to the sensing of gaseous components in an automotive exhaust system.

BACKGROUND ART

In recent years, air pollution created by internal combustion engines such as used in automobiles has become of great concern. This has led to the passage of air pollution control laws which require automobile manufacturers to reduce the emission of harmful materials from automotive engines. Typical of the pollutants to be controlled are hydrocarbon emission, carbon monoxide emission and nitrous oxide emission.

Automotive manufacturers have introduced the catalytic converter to control these emissions. However, the effective operation of the catalytic converter is dependent upon maintaining a proper level of oxygen in the engine exhaust gas resent in the catalytic converter. This has led the automotive industry to develop an accurate, yet inexpensive oxygen sensor for use in the catalytic converter.

One type of oxygen sensor that has been developed for use with catalytic converters includes a ceramic sensor, typically formed of zirconium oxide. The sensor can be formed into many shapes, but is typically in the shape of a tube or cone with an outer electrode on the outer surface of the sensor and inner electrode on the interior surface of the sensor. The outer surface of the sensor is exposed to the exhaust gas. The interior of the sensor is exposed to the atmosphere. Charged oxygen ions can migrate through the sensor ceramic at a rate depending upon the relative content of oxygen in the exhaust gas and the atmosphere. The migration of the charged oxygen ions generates a potential between the inner and outer electrodes which is proportional to the oxygen content in the exhaust gas.

Various designs have been proposed for such an oxygen sensor. U.S. Pat. No. 3,844,920, issued to Burgett, et al. on Oct. 29, 1974, discloses an air-fuel ratio sensor. A zirconia element 20 is employed with an inner electrode 33 and an outer electrode 35. The inner electrode 33 is electrically connected through a metal gasket 42 to a body member 37. A centerbore 45 in the body member 37 permits air into the hollow zirconia element 20. A metal gasket 28 is positioned between shoulder 27 on element 20 and shoulder 14 on shell member 12.

U.S. Pat. No. 3,847,778, issued to Riddel on Nov. 12, 1974, discloses an air-fuel ratio sensor. No apparent seal is provided to isolate the inner electrode on zirconia cell 30 from the exhaust gases.

U.S. Pat. No. 3,960,693, issued to Weyl, et al. on June 1, 1976, discloses a device for electrochemically measuring the concentration of oxygen in combustion gases. The device disclosed includes a tubular member 11 of an ion-conducting solid electrolyte material, such as zirconium dioxide. A terminal member 16 having an annular bead 17 is in electrical contact with the interior layer 14 on tubular member 11. An electrically conductive glass melt 19 and a metallic annular member 20 secure the member 16 within the interior of the member 11. The member 16 is hollow and has air inlet openings 22 which permit the atmosphere to communicate with the interior of the tubular member 11. The end of the terminal member 16 distant from tubular member 11 is provided with a plug-in terminal 21. Rings 31 and 34 are positioned between the housing 23 and tubular member 11 for a seal.

U.S. Pat. No. 4,132,615, issued to Linder, et al. on Jan. 2, 1979, discloses an internal combustion engine exhaust gas oxygen sensor and catalyzer combination. The patent discloses a contact flag 10 with a bore 13 to provide ambient air into the hollow interior of an electrolyte tube 3. The contact flag 10 is mechanically secured in the end portion 4 of the tube 3 and is in electrical contact with the inner electrode 6 formed in the tube 3. A press connection 9 provides for mechanical holding of the contact flag 10 and, likewise, for electrical connection thereof with the inner electrode 6. A steel ring 11 protects the end of the melted end press 9, and is used to compress the electrically conductive connection 9 so that the melt 9 will provide good electrical contact between the electrode 6 and contact flag 10. Press 9 and steel ring 12 are positioned between tube 3 and socket 7.

U.S. Pat. No. 4,169,778, issued to Mann, et al. on Oct. 2, 1979, discloses a heated solid electrolyte oxygen sensor. The sensor includes a solid electrolyte tube 12 and an electrode terminal member 14. Member 14 includes a central tubular portion 14a and a circumferential flange 14b at its lower end for contact with a sealing ring 30. The sealing ring 30, in turn, contacts the inner electrode 58 on the electrolyte tube 12. Conductive coating 58b can be a stripe across the end face of the electrolyte tube 12 or be a continuous circumferential coating. The electrode terminal member 14 includes an aperture 74 which permits air entering the annular passage 68 to contact the inner electrode 58. Exhaust gas leaking past sealing ring 32 could reach aperture 74 as washer 20 is only a flat mica washer. U.S. Pat. No. 4,175,019 and No. 4,178,222 disclose a similar design.

U.S. Pat. No. 4,222,840 issued to Murphy, et al on Sept. 16, 1980, shows no apparent way for air to enter the cavity above upper electrode 18 of disc 12.

None of these designs has proven totally satisfactory. Ideally, the oxygen sensor should provide significant sealing protection to prevent exhaust gases from entering the interior zone of the ceramic sensing element to prevent spurious oxygen content measurements. Naturally, when an engine is started, the sensor will rapidly rise from ambient temperature to its normal operating temperature of between 700° and 1000° F. The sealing must be effective during this rapid temperature rise and thereafter. Therefore, any sealing design must account for the significant thermal expansion encountered in the sensor as the rapid temperature rise to operating conditions takes place, yet perform the function inexpensively.

SUMMARY OF THE INVENTION

In accordance with one aspect of the present invention, an exhaust gas sensor is provided for sensing the oxygen content in the exhaust system relative to the oxygen content of air. The exhaust gas sensor includes a sensor element having a generally conical shape with one closed end and one open end surrounded by an annular surface. The sensor element has an outer electrode formed on the exterior surface of the sensor element and an inner electrode formed on the interior surface of the sensor element extending to the annular surface. An electrode is provided in the form of an elongate hollow tube and a sealing disk. Both the hollow tube and sealing disk are electrically conductive. The hollow tube is provided with a first opening at one end thereof and a second opening at the other end thereof. The sealing disk is positioned along the hollow tube adjacent the first end. The sealing disk is employed for sealing engagement with the annular surface of the sensor element for insuring that the only gases present in the interior of the sensor element enter the second end of the hollow tube and pass through the hollow tube to the sensor element. In accordance with another aspect of the present invention, the sealing disk contacts the annular surface of the sensor element about the entire periphery of the annular surface to enhance the electrical connection between the sealing disk and the inner electrode.

BRIEF DESCRIPTION OF THE DRAWINGS

A more complete understanding of the invention may be had by reference to the following Detailed Description when taken in conjunction with the accompanying Drawings, wherein.

DETAILED DESCRIPTION

Figure 1:
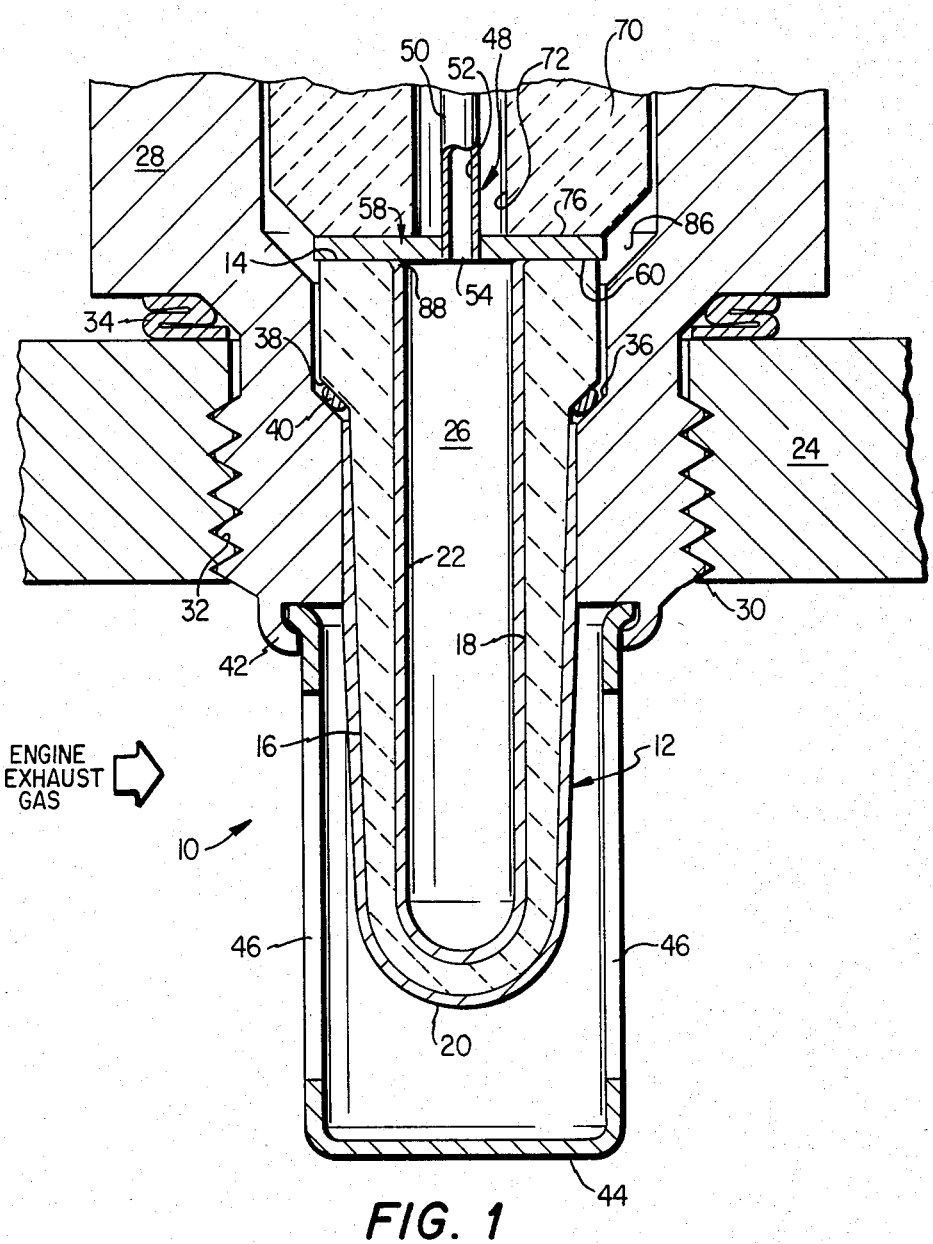
FIG. 1 is a vertical cross-sectional view of the exhaust gas sensor of the present invention illustrating the sensor element and electrode.
Figure 2:
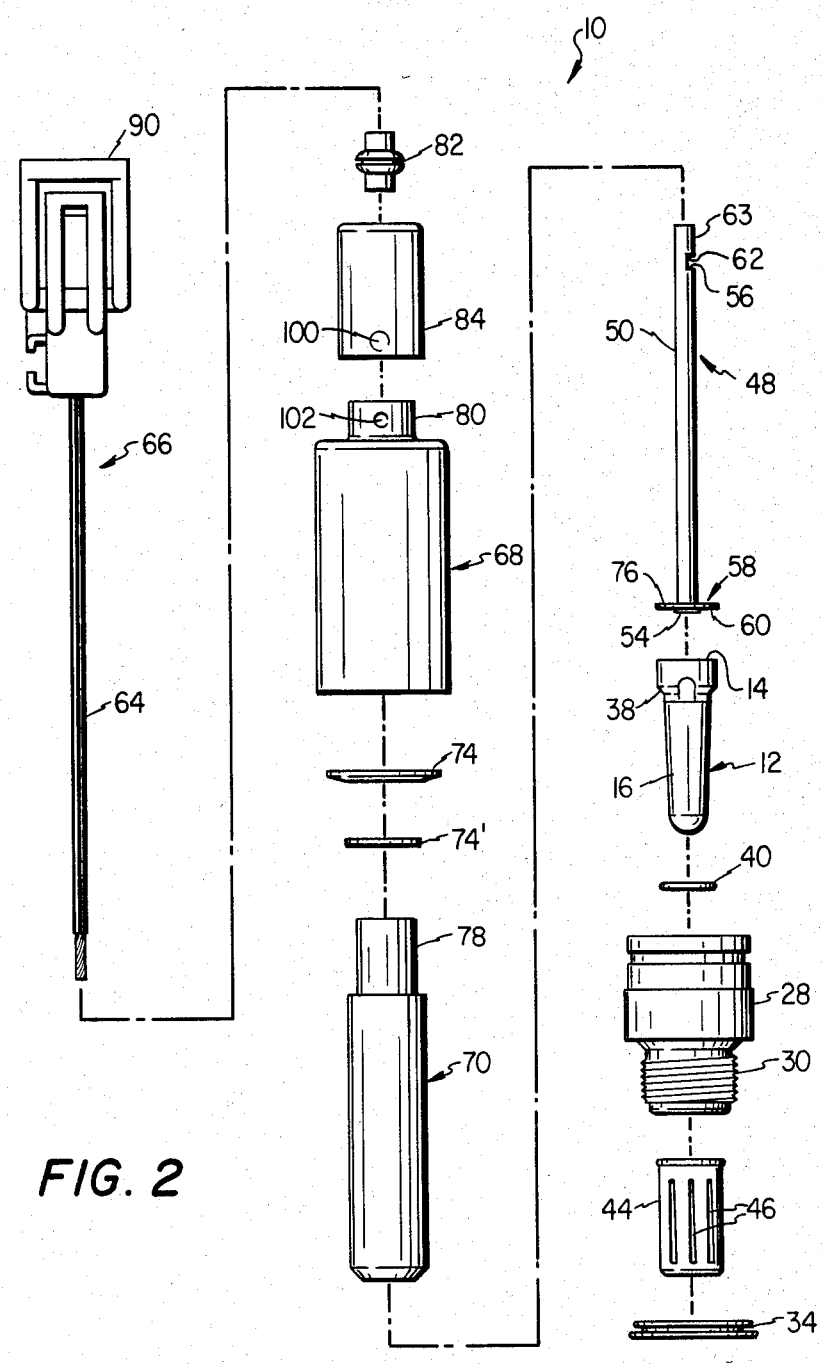
FIG. 2 is an exploded view of the exhaust gas sensor.

Referring now to the Drawings, wherein like reference characters designate like or corresponding parts throughout several views, FIGS. 1 and 2 illustrate an exhaust gas sensor 10 forming one embodiment of the present invention.

The exhaust gas sensor 10 includes a sensor element 12 as best seen in FIG. 1. The sensor element 12 has a generally conical shape with one closed end and one open end surrounded by a planar annular surface 14. The sensor element 12 permits the passage of charged oxygen ions between the exterior surface 16 and interior surface 18 thereof. The sensor element 12 is preferably formed of zirconium as further described in pending U.S. patent application Ser. No. 592,625, filed Mar. 23, 1984 and U.S. Pat. No. 4,493,746, issuing on Jan. 15, 1985, both filed simultaneously with this application and naming the same inventive entity as this application. Both applications are assigned to the common assignee of the present application. These applications are hereby incorporated by reference herein. Outer electrode 20 is formed on the exterior surface 16 as seen in FIG. 1. An inner electrode 22 is formed on the interior surface 18. Preferably, the electrodes 20 and 22 are formed of platinum. The sensor element 12 is supported within an exhaust passage 24 so that the exterior surface 16 thereof is exposed to the exhaust gases within the exhaust passage. The interior 26 of the sensor element 12 is exposed to air. The flow of charged oxygen ions between the surfaces 16 and 18 therefore is indicative of the relative oxygen content of the exhaust gas within the exhaust passage 24.

In operation, a voltage is generated between the outer electrode 20 and inner electrode 22 by the migration of free oxygen ions when the concentration of oxygen differs between the air in the interior 26 and the exhaust gas within the catalytic converter 24. Typically, the inner electrode 22 will be positive relative to the outer electrode 20 in normal operation. The outer electrode 20 can then be grounded to the exhaust passage 24 as most vehicles made today are negative ground. The inner electrode 22 is connected to appropriate electronic circuitry by a lead assembly. The electronic circuitry will compute the oxygen content in the exhaust gas from the signal of the exhaust gas sensor 10 and adjust engine operation to optimize the oxygen content for effective operation of the catalytic converter.

A housing 28 is provided which includes a portion having threads 30. The threads 30 are adapted for threaded engagement with corresponding threads 32 in the exhaust passage 24. A conventional seal 34, of the type commonly used to seal a spark plug to the head of an engine, seals between the housing 28 and the exhaust passage 24. The interior of housing 28 is formed with a conical shoulder 36. The sensor element 12 also is provided with a conical shoulder 38 which faces the shoulder 36 when the exhaust gas sensor 12 is assembled. An airtight electrically conductive seal 40 is positioned between the shoulders 36 and 38 to provide a gastight seal therebetween and provide an electrical connection between outer electrode 20 and housing 28. Preferably, the seal 40 is formed of a beryllium copper.

The lower end of the housing 28 is provided with inwardly turned lips 42 which secure a gas deflector 44 thereto. The gas deflector 44 includes shaped apertures 46, such as seen in FIG. 2, to admit the exhaust gases about the exterior surface 16 of the sensor element 12.

A member 48 is provided which performs both the function of electrically connecting the inner electrode 22 to the exterior of exhaust gas sensor 10 and seal against the sensor element 12 to resist the entry of exhaust gas into the interior 26 of the sensor element 12 which could result in an incorrect sensing of the oxygen content within the exhaust gas. The member 48 includes a hollow tube 50 which has a through aperture 52 which opens at a first end 54 and a second end 56. Adjacent the first end 54, a seal disk 58 is secured about the outer surface of the hollow tube 50. As can be seen in FIG. 1, when the member 48 is properly positioned relative to the sensor element 12, the planar annular lower surface 60 of the seal disk 58 will be in intimate contact with the planar annular surface 14 of the sensor element 12. This will provide a gastight seal between the annular surfaces 14 and 60. A notch 62 and crimping portion 63 are provided in tube 50 near the second end 56 which form a wire crimp for crimping the wire 64 from a lead assembly 66 which can be used to connect the exhaust gas sensor 10 to electronic circuitry used to interpret the signals provided by the gas sensor 10 to evaluate the oxygen content of the exhaust gas. With notch 62, the crimping portion 63 can be crimped about wire 64 to secure it to member 48 without crimping the second end which could lead to reduced air flow to interior 26.

A cover 68, seen in FIG. 2, is secured to the housing 28. A ceramic insulator 70 having a hollow core 72 is positioned within the cover 68 and extends within the housing 28 as seen in FIG. 1. A spring washer 74 acts between the cover 68 and ceramic insulator 70 to urge the ceramic insulator 70 downward, as seen in FIG. 1, into abutting contact with the planar annular upper surface 76 of the member 48. This urges the planar annular lower surface 60 of the member 48 into sealing contact with the annular surface 14 of the sensor element 12 and further acts to urge the shoulders 36 and 38 into sealing engagement with the seal 40. In the preferred embodiment, the spring washer 74 comprises a belleville washer. In the preferred embodiment, the belleville washer provides about 700 pounds of pressure to force the ceramic insulator 70 against the member 48.

If desired, a second spring washer 74' can be used to assist spring washer 74. One washer can be designed for coarse tuning of the force between member 48 and sensor element 10 while the other can be used to fine tune the force. Spring washer 74' would also preferably be a belleville washer.

The ceramic insulator has a reduced diameter portion 78 which passes through and extends out of a reduced diameter portion 80 of the cover 68. A vent cap housing 84 is provided with a rubber grommet 82 to resist the entry of water from outside sensor 10. The inner end of grommet 82 can touch the end of crimping portion 63 without reducing air flow through member 48 because the second end 56 remains unobstructed. The wire 64 passes through the grommet 82. Vent cap housing 84 has three small inward dimples or standoffs 100 which are resiliently received in three corresponding holes 102 in cover 68 to secure housing 84 on cover 68. The standoffs 100 and holes 102 are designed to provide a small clearance (preferably 0.002") between the outer diameter of portion 80 and the inner diameter of housing 84 to provide openings between housing 84 and cover 68 for air to enter the second end 56. Finally, the wire 64 extends from its electrical connection with the member 48 to a connector clip 90 for connection to the electronic circuitry employed with the exhaust gas sensor 10.

Naturally, the exhaust gas sensor 10 will be at ambient temperature prior to starting the engine. However, once the engine is started, the temperature of the exhaust passage 24 and the exhaust gas sensor 10 will rise rapidly to its operating temperature of between 700° and 1000° F. To provide an accurate measurement of the oxygen content in the exhaust gas, it is necessary to form effective seals between the interior of the exhaust passage 24 and the interior 26 of sensor element 12 despite this rapid elevation in temperature and corresponding thermal expansion of elements within the exhaust gas sensor 10. As one method to enhance this seal, the housing 28, gas deflector 44, member 48, cover 68 and vent cap housing 84 are all formed of stainless steel. In the preferred embodiment, a 430 stainless steel is used. Because of the temperature extremes, use of a cold rolled or soft iron materials would gall into the exhaust pipe.

The design of the exhaust gas sensor 10 also provides effective sealing of the interior 26 of sensor element 12 from exhaust gas. If exhaust gas leaks past seal 40 into cavity 86, the seal between member 48 and sensor element 12 will prevent the exhaust gas from entering interior 26. In addition, any gas in the cavity 86 would merely flow past the outer surface of the ceramic insulator 70 and escape to the atmosphere without being permitted to approach the second end 56 of the member 48 since second end 56 extends well into housing 84 and the clearance between the housing 84 and cover 68 is positioned between second end 56 and the sensor element 10.

The member 48 also provides an additional enhancement of electrical contact with the inner electrode 22. The inner electrode 22 extends to the annular surface 14 and forms a ring 88 which extends around the entire inner periphery of the annular surface 14. The lower surface 60 of the member 48 can therefore contact the inner electrode 22 about the entire 360° circumference of the ring 88. In past designs, contact between an inner electrode and another electrode extending outside an exhaust gas sensor have not permitted contact for more than 270° about the end of the inner electrode. Therefore, since in any given situation an exterior electrode such as member 48 may only contact an inner electrode at certain points, the likelihood of contact is enhanced by providing for contact about the full 360° extent of the end of the inner electrode formed by ring 88.

Although only a single embodiment of the invention has been illustrated in the accompanying drawings and described in the foregoing Detailed Description, it will be understood that the invention is not limited to the embodiment disclosed, but is capable of numerous rearrangements, modifications and substitutions of parts and elements without departing from the spirit of the invention.

I claim:

1. An exhaust gas sensor for sensing the oxygen content in an exhaust system relative to the oxygen content of air, comprising:

a solid electrolyte sensor element having a generally conical shape with one closed end and one open end surrounded by an annular surface, the sensor element having an outer electrode formed on the exterior surface of the sensor element and an inner electrode formed on the interior surface of the sensor element extending to the annular surface;

a housing for supporting said sensor element and having a conical shoulder;

an electrically conductive seal for sealing engagement between the conical shoulder on the housing and the outer electrode of the sensor element;

a member forming an enclosed elongate hollow tube and a sealing disk, both the elongate hollow tube and the sealing disk being electrically conductive, the hollow tube having an opening at the first end thereof and an opening at the second end thereof, the opening at the second end thereof being a notch through the wall of the hollow tube, the hollow tube extending beyond the notch forming a crimping portion having a wire crimped therein to connect the inner electrode of the exhaust gas sensor to the wire, the sealing disk being positioned on the hollow tube adjacent the first end for sealing engagement with the annular surface of the sensor element for insuring that the only gases present in the interior of the sensor element enter the second end of the hollow tube and pass through the hollow tube to the sensor element;

a cover secured to the housing, the second end of the hollow tube extending out of the cover;

means for urging the sealing disk into contact with the inner electrode so that sealing contact is made between the member and the annular surface of the gas sensor and between the conical shoulder of the housing and outer electrode through said electrically conductive seal; and a vent cap housing secured to the cover with at least one gap between the cover and vent cap housing to admit air into the interior of the vent cap housing, the second end of the hollow tube being within the interior of the vent cap housing with said at least one gap positioned between said second end of the hollow tube and the electrically conductive seal between the housing and the outer electrode to reduce the potential for contamination of the air within the hollow tube with exhaust gas.

2. The exhaust gas sensor of claim 1 wherein said sealing disk contacts the annular surface about the entire periphery thereof to enhance the electrical connection between the sealing disk and the inner electrode.

3. The exhaust gas sensor of claim 1 wherein the inner electrode in the sensor element extends to define an annular ring at the annular surface of the sensor element, the seal disk of said member being positioned for electrical contact with the inner electrode about the entire circumference thereof.

4. The exhaust gas sensor of claim 1 wherein said means for urging comprises at least one belleville washer.

5. An exhaust gas sensor for sensing the oxygen content in an exhaust system relative to the oxygen content of air, comprising:

a solid electrolyte sensor element having a generally conical shape with one closed end and one open end surrounded by an annular surface, the sensor element having an outer electrode formed on the exterior surface of the sensor element and an inner electrode formed on the interior surface of the sensor element extending to the annular surface, said sensor element having a conical shoulder;

a housing for supporting said sensor element and having a conical shoulder, said housing further having a threaded portion and an inwardly turned lip;

an electrically conductive seal for sealing engagement between the conical shoulder on the housing and the sensor element;

a gas deflector for engagement with the lip on said housing, said gas deflector having apertures therein to permit the exhaust gases to contact the exterior surface of the sensor element;

a member forming an enclosed elongate hollow tube having a through aperture opening at first and second ends and a sealing disk, both the hollow tube and sealing disk being electrically conductive, the sealing disk being positioned along the hollow tube adjacent the first end for simultaneous sealing engagement with the annular surface of the sensor element and electrical contact with the inner electrode, the opening of said aperture at the second end of the hollow tube being formed by a notch in the wall of the hollow tube, a portion of the hollow tube forming a crimping portion to crimp a wire therein to connect the inner electrode of the exhaust gas sensor to the wire the crimping portion being crimped to the wire without interfering with the opening through the notch;

a ceramic insulator having a hollow core, one end of the ceramic insulator contacting the surface of the sealing disk opposite the annular surface of the sensor element;

a cover secured to said housing, the second end of the hollow tube extending out of the cover;

means for acting between the housing and the ceramic insulator to urge the ceramic insulator into contact with the sealing disk so that sealing contact is made between the member and the annular surface of the sensor element and between the conical shoulders of the sensor element and housing through said electrically conductive seal; and a vent cap housing secured to the cover, at least one gap being formed between the cover and vent cap housing to permit air onto the interior of the vent cap housing, the second end of the hollow tube being within the vent cap housing with said gap being between the second end of the hollow tube and the electrically conductive seal to reduce the potential for exhaust gas entering the hollow tube, exhaust gas leaking past the conductive seal being vented through said at least one gap.

6. The exhaust gas sensor of claim 5 wherein said means for acting between the housing and the ceramic insulator comprises at least one belleville washer.

* * * * *

UNITED STATES PATENT AND TRADEMARK OFFICE
CERTIFICATE OF CORRECTION

PATENT NO. : 4,526,672

DATED : July 2, 1985

INVENTOR(S) : Larry T. Reed

It is certified that error appears in the above-identified patent and that said Letters Patent is hereby corrected as shown below:

Column 1, line 22, change "resent" to --present--.

Column 8, line 27, change "onto" to --into--.

Signed and Sealed this

Twelfth Day of November 1985

[SEAL]

Attest:

Attesting Officer

DONALD J. QUIGG

Commissioner of Patents and Trademarks